United States Patent

Heuer et al.

[11] Patent Number: 6,025,499
[45] Date of Patent: Feb. 15, 2000

[54] PROCESS FOR THE PREPARATION OF A NITROPYRAZOLE AMIDE

[75] Inventors: Lutz Heuer, Dormagen; Nikolaus Müller, Monheim; Guido Steffan, Odenthal, all of Germany

[73] Assignee: Bayer Aktiengesellschaft, Leverkusen, Germany

[21] Appl. No.: 09/276,577

[22] Filed: Mar. 25, 1999

Related U.S. Application Data

[62] Division of application No. 08/888,889, Jul. 7, 1997.

[30] Foreign Application Priority Data

Jul. 17, 1996 [DE] Germany .......................... 196 28 778
Aug. 16, 1996 [DE] Germany .......................... 196 32 920

[51] Int. Cl.[7] ................................................. C07D 231/16
[52] U.S. Cl. ............................................................ 548/371.7
[58] Field of Search ............................................ 548/371.7

[56] References Cited

U.S. PATENT DOCUMENTS

| | | | |
|---|---|---|---|
| 4,145,554 | 3/1979 | Jones et al. ............................... | 548/377 |
| 4,172,136 | 10/1979 | Berger et al. ..................... | 548/371.7 X |
| 4,282,361 | 8/1981 | Hect et al. ............................ | 548/371.7 |
| 4,317,823 | 3/1982 | Rainer .................................. | 424/248.54 |
| 4,810,283 | 3/1989 | Gehring et al. .................. | 548/371.7 X |

FOREIGN PATENT DOCUMENTS

| | | | |
|---|---|---|---|
| 0463756 | 1/1992 | European Pat. Off. .................... | 487/4 |
| 0526004 | 2/1993 | European Pat. Off. .................... | 487/4 |
| 3029281 | 2/1981 | Germany .................................... | 487/4 |

OTHER PUBLICATIONS

Chemical Abstracts, vol. 52, No. 1, Jan 10, 1958, Columbus, Ohio, US; Robins, et al.: "Potential purine and antagonists . . . ", Spalte 395; XP002047057 & J. Org. Chem., 21, 833–836 (1956), *Zusammenfassung*.

Musante, pp. 121–123 (1945) Gazz Chim Ital 25.

J. Wierzchowski, et al., Analogues of formycins A and B: synthesis and some properties of methyl derivatives of 7–amino and 7–keto pyrazolo(4,3–d)pyrimidines*, Acta Biochimica Polonica, vol. 27, No. 1, pp. 35–56, (1980).

P. Giovanii Baraldi, et al. synthesis and Anti Tumor Acivity of a New Class of Pyrazolo[4–3–e]pyrrolo [1,2–a][1,4] diazepinone Analouges of Pyrrolo [1,4][2,1–c]benzodiazepines, J. Med. Chem., vol. 37, No. 25, pp. 4329–4337 (1994).

G.L. Ellames, et al., The Syntheses fo Acycloformycins and 5–Amino–3–(2–hydroxyethoxy)–methylpyrazolo [4,3–d] pyrimidin–7(6H)–one,m an Analogue of the Antiviral Acycolguanosine, J. Chem. Soc., Perkin. Trans. I, pp. 2087–2091, (1995).

Musante, Su alcuni acidi pirazolcarbonici e loro derivati, pp. 121–136, Gazz Ital. Chim, 57 (1945).

*Primary Examiner*—Robert W. Ramsuer
*Attorney, Agent, or Firm*—Norris, McLaughlin & Marcus

[57] ABSTRACT

Nitropyrazole amides of the formula (I)

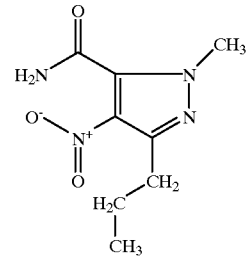

are prepared by reacting nitropyrazole esters of the formula (II)

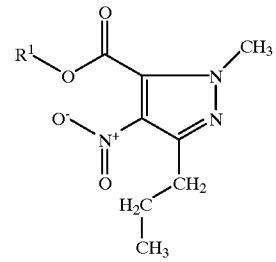

with ammonia.

3 Claims, No Drawings

PROCESS FOR THE PREPARATION OF A NITROPYRAZOLE AMIDE

This application is a division of Ser. No. 08/888,889 filed Jul. 7, 1997.

The present invention relates to new nitropyrazole esters, a process for their preparation by nitration of corresponding pyrazole esters and their use as intermediates for the preparation of a known nitropyrazole amide which, for its part, is an intermediate for the preparation of pharmaceutical active compounds.

It is known that alkyl-substituted nitropyrazole esters differing from the nitropyrazole esters according to the invention can be prepared by esterification of the corresponding acids or by alkylation of non-alkylated nitropyrazole esters (see DE-A 30 29 281, Gazz. Chim. Ital. 75, 121 to 130 (1945), J. Med. Chem. 37 4329 to 4337 (1994) and Acta Biochem. Pol. 27, 35 to 56 (1980)).

The disadvantage of these processes is that they only lead to the target by a circuitous route, pyrazolecarboxylic acid first having to be prepared and isolated, then esterified and then nitrated or processed in the reverse sequence.

It is furthermore known that the nitropyrazole amide of the formula (I)

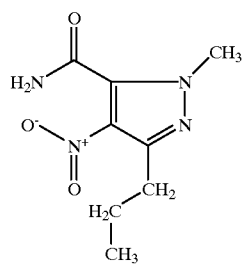

(I)

can be prepared from the corresponding pyrazolecarboxylic acid by nitration, formation of the acid chloride and reaction with ammonia (see EP-A 0 463 756). The pyrazolecarboxylic acid, for its part, is obtained by hydrolysis of a corresponding ester which occurs as an intermediate.

This process too is multi-stage and involved.

Nitropyrazole esters have now been found of the formula (II)

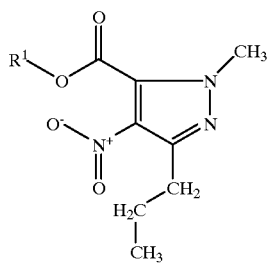

(II)

in which
$R^1$ represents $C_1$–$C_6$-alkyl.

In formula (II), $R^1$ preferably represents methyl, ethyl, n-propyl, i-propyl, n-butyl, i-butyl or sec-butyl.

The present invention also relates to mixtures of two or more nitropyrazole esters of the formula (II), in which the individual components can be present in any desired proportions to one another.

The present invention furthermore relates to a process for the preparation of nitropyrazole esters of the formula (II), which comprises nitrating pyrazole esters of the formula

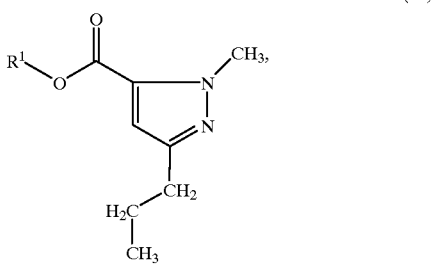

(III)

in which
$R^1$ has the meaning indicated under formula (II).

Pyrazole esters of the formula (III) are known and accessible in a known manner or analogously thereto (see, for example, EP-A 463 756, C.A. 123, 198 791 (1995), C.A. 114, 185 497 (1991), EP-A 526 004 and CAS-No. 133 261-07-1).

The nitration can be carried out, for example, using a mixture, having a nitrating action, of nitric acid and sulfuric acid only using nitric acid or by introduction of an inorganic nitrate into sulfuric acid. When using mixtures of nitric and sulfuric acid, these can be present, for example, in the weight ratio of nitric acid to sulfuric acid of 99.9:0.1 to 1:99, preferably 90:10 to 10:90.

The nitrating agent can be employed, for example, in the stoichiometrically required amount or in an excess, for example up to a 50-fold excess. 1.1- to 10-fold of the stoichiometrically required amount is preferably employed.

It is advantageous to employ nitrating agents having a water content which is as low as possible. The water content is, for example, below 10% by weight, preferably between 0 and 5% by weight.

The nitration can be carried out, for example, at temperatures in the range −30 to +100° C. It is preferably carried out at −10 to +70° C., particularly preferably at 0 to +60° C.

The reaction time depends on the temperature in such a way that at higher temperatures, shorter reaction times can be selected. It can be, for example, between 20 minutes and 24 hours. Reaction times between 1 and 10 hours are preferred.

The nitration can be carried out with or without the addition of a solvent. For reasons of better manipulability of the reaction mixture, the addition of a solvent is preferred. Suitable solvents are those which cannot be nitrated under the conditions used. Examples are sulfuric acid, oleum, o-dichlorobenzene, dinitro-benzenes, dichloromethane and dichloroethane.

If it is desired to isolate the nitropyrazole esters of the formula (II) prepared, the completely reacted nitration mixture can, for example, be discharged onto ice and/or water, then extracted with a water-immiscible solvent and the extract freed from the solvent.

The present invention also relates to the use of nitropyrazole esters of the formula (II) for the preparation of the nitropyrazole amide of the formula (I) by reacting nitropyrazole esters of the formula (II) with ammonia. This use can also be described as a process for the preparation of the nitropyrazole amide of the formula (I), which comprises reacting nitropyrazole esters of the formula (II) with ammonia.

The reaction with ammonia can be carried out, for example, using aqueous or gaseous ammonia, at, for example, 0 to 250° C. and, for example, in an open reactor or in a closed autoclave under pressures up to, for example, 50 bar. Preferred reaction conditions are temperatures in the range 20 to 120° C., in particular 30 to 100° C., and pressures from normal pressure up to the pressure of the reaction system which is established by itself in an autoclave at the respective reaction temperature.

Ammonia can be employed, for example, in amounts between the stoichiometrically required amount and a 50-fold excess thereof. A 1.2–20-fold amount of the stoichiometrically required amount is preferred.

The reaction with ammonia can be carried out with or without the addition of a solvent. It is preferably carried out with addition of an inert organic solvent. Examples of these are: alcohols such as methanol, ethanol, propanol and butanols, aromatics such as benzene, toluene, chlorobenzene and dichlorobenzenes, and sulfoxides such as dimethyl sulfoxide. Solvent mixtures can also be employed.

As catalysts for the reaction with ammonia there can optionally be used bases, for example in amounts of from 0.05 to 5 mol %. Suitable are for example alcoholates such as potassium tertiary butylate, sodium methylate, sodium ethylate, sodium isopentanoate and sodium isopropylate as well as other bases such as DABCO, sodium hydroxide, potassium hydroxide, sodium carbonate, potassium carbonate, DBU, DBM and triethylene amine.

The nitropyrazole amide of the formula (I) prepared can, for example, be isolated from the reaction mixture present after the reaction with ammonia by stripping off the volatile components of the reaction mixture in vacuo.

In a particular embodiment, pyrazole esters of the formula (III) are reacted with an only just adequate amount or a small excess of nitrating agent and the reaction with ammonia is then carried out without intermediate isolation.

The nitropyrazole amide of the formula (I) prepared according to the invention via the intermediate stage of nitropyrazole esters of the formula (II) can be used as nitropyrazole amide of the formula (I) obtained in another manner, for example for the preparation of active compounds (see, for example, EP-A 463 756).

The new nitropyrazole esters of the formula (II) can be obtained in one stage from corresponding pyrazole esters of the formula (III) and make the nitropyrazole amide of the formula (I) likewise accessible in one stage. The synthesis route to the nitropyrazole amide of the formula (I) is shortened compared with the prior art, the space-time yields achievable are improved and smaller amounts of reagents and energy are needed than previously. It is surprising that these advantageous effects can be realized using the relatively uncomplicated process according to the invention, since the profession has previously only taken into account complicated processes for the preparation of the nitropyrazole amide of the formula (I).

EXAMPLES

Example 1

193.7 g of a mixture of 33.3% by weight concentrated nitric acid and 66.7% by weight concentrated sulfuric acid were slowly added dropwise at 45° C. to a solution of 86.1 g of 89% strength by weight ethyl 1-methyl-3-propyl-5-pyrazolecarboxylate (A) in 330 ml of concentrated sulfuric acid. The mixture was stirred for a further 3 hours, then cooled to room temperature and added to 2 kg of ice-water. The mixture then present was extracted with toluene. After drying the toluene phase at 50° C. in vacuo, 102 g of a pale yellow oil were obtained, which was ethyl 1-methyl-3-propyl-4-nitro-5-carboxylate (B). This corresponds to a yield of 97% of theory.

Example 2

85 g of gaseous ammonia were injected at 50° C. into a solution of 120 g of 89% strength by weight ethyl 1-methyl-3-propyl-4-nitro-5-pyrazolecarboxylate in 400 ml of ethanol in an autoclave. The reaction mixture was stirred for a further 3 hours and then, by stripping off the solvent, 103 g of 1-methyl-3-propyl-4-nitro-5-carboxamide (C) were obtained as colorless needles having a melting point of 140° C.

Example 3

Within one hour 50 g of (A) and 92.5 g of sulfuric acid were added dropwise to a mixture of 62 g sulfuric acid, 33.7 g of 20% by weight oleum and 65 g of nitric acid. The mixture was stirred for additonal 60 minutes and then was worked up as in Example 1. There were obtained 52.2 g of (B).

Example 4

50 g of (B), 14.5 g of ammonia and 110 g of ethanol were stirred for 20 hours at 50° C. and worked up as described in Example 2. There were obtained 37.3 g of (C).

What is claimed is:

1. A process for the preparation of the nitropyrazole amide of the formula

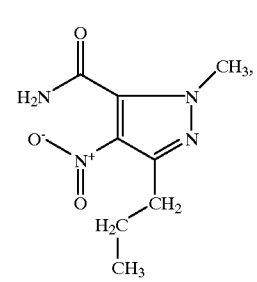

(I)

which comprises reacting a nitropyrazole ester of the formula

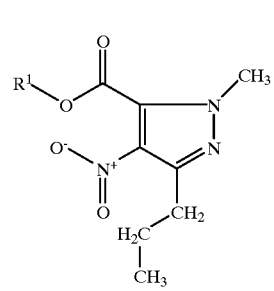

(II)

in which

R$^1$ represents C$_1$–C$_6$-alkyl with ammonia.

2. A process as claimed in claim 1, wherein the reaction with ammonia is carried out using aqueous or gaseous ammonia at 0 to 250° C. and pressures up to 50 bar.

3. A process as claimed in claim 2, wherein ammonia is employed in amounts from the stoichiometrically required amount up to a 50-fold excess thereof and a solvent is added.

* * * * *